United States Patent
Hay et al.

(10) Patent No.: US 6,549,005 B1
(45) Date of Patent: Apr. 15, 2003

(54) MAGNETIC DETECTION OF DISCONTINUITIES IN RAILWAY RAILS USING HALL EFFECT SENSORS

(75) Inventors: Sid Hay, Bentley (AU); Robert Street, Bentley (AU); Robert Gordon Vanselow, Karratha (AU)

(73) Assignee: Technological Resources Pty. Ltd., Melbourne (AU)

( * ) Notice: Subject to any disclaimer, the term of this patent is extended or adjusted under 35 U.S.C. 154(b) by 0 days.

(21) Appl. No.: 09/180,966

(22) PCT Filed: May 16, 1997

(86) PCT No.: PCT/AU97/00303

§ 371 (c)(1),
(2), (4) Date: Jun. 1, 1999

(87) PCT Pub. No.: WO97/44654

PCT Pub. Date: Nov. 27, 1997

(30) Foreign Application Priority Data

May 17, 1996 (AU) ............................................. PN 9925

(51) Int. Cl.[7] ........................ G01N 27/82; G01N 27/83; G01R 33/07

(52) U.S. Cl. ........................ 324/217; 324/235; 324/242; 324/225

(58) Field of Search ................................ 324/217, 235, 324/242, 251, 225, 238, 220, 243, 244, 240, 233

(56) References Cited

U.S. PATENT DOCUMENTS

| | | | |
|---|---|---|---|
| 1,998,952 A | * 4/1935 | Edgar et al. ................. | 324/217 |
| 2,031,469 A | 2/1936 | Drake ......................... | 175/183 |
| 2,060,458 A | * 11/1936 | Billstein ...................... | 175/183 |
| 2,540,870 A | 2/1951 | Farmer ........................ | 175/183 |
| 2,602,840 A | 7/1952 | McKee et al. ............... | 175/183 |
| 2,740,090 A | * 3/1956 | Dionne ........................ | 324/217 |
| 2,869,073 A | 1/1959 | McKee et al. ................ | 324/37 |
| 2,958,818 A | * 11/1960 | Cowan et al. ............... | 324/217 |
| 4,814,705 A | 3/1989 | Saunderson ................. | 324/225 |
| 5,336,998 A | 8/1994 | Watts et al. ................. | 324/235 |

FOREIGN PATENT DOCUMENTS

| JP | 08248002 | 9/1996 |
|---|---|---|
| WO | 97/03353 | 1/1997 |

OTHER PUBLICATIONS

Damento et al, (Investigation of local Events of Magnetization Reversal in a Nd–Fe–B magnet by use of a Hall-Effect Microprobe, May 3, 1987, 1877–1878.*

* cited by examiner

Primary Examiner—Walter E. Snow
(74) Attorney, Agent, or Firm—Michael Best & Friedrich LLP

(57) ABSTRACT

A method and apparatus for high speed magnetic detection of surface fatigue cracks in railway rails. The magnetic material of the rail is magnetized by touch magnetization using a permanent magnet (31), leaving a remanent magnetic field. A sensor head (30, 50) having a plurality of Hall effect sensors (32) senses stray flux generated in the vicinity of surface fatigue in the rail head by the remanent magnetic field. The sensor head (30, 50) may incorporate a proximity sensor (60) to compensate for variations in sensor height. The apparatus may be mounted on a conventional track recording vehicle (TRV) for use in routinely monitoring the surface fatigue severities in rail along a railway.

8 Claims, 7 Drawing Sheets

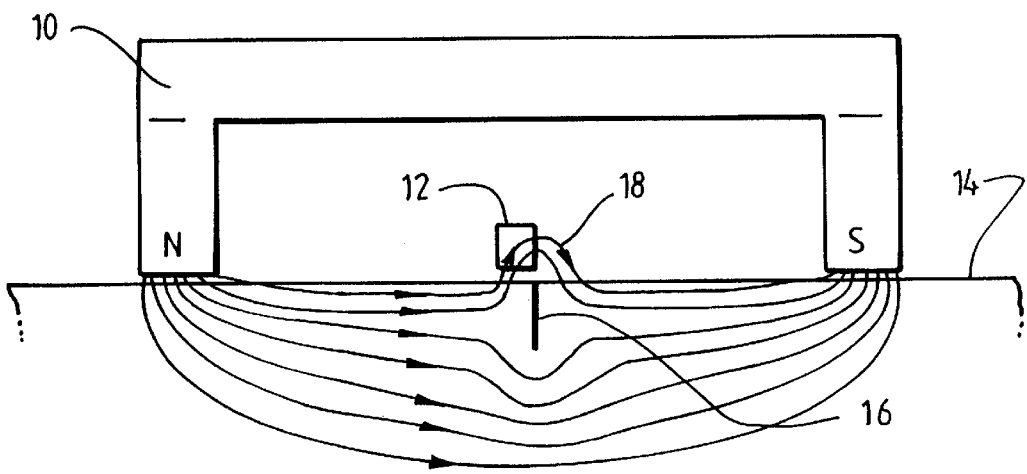
FIG. 3.
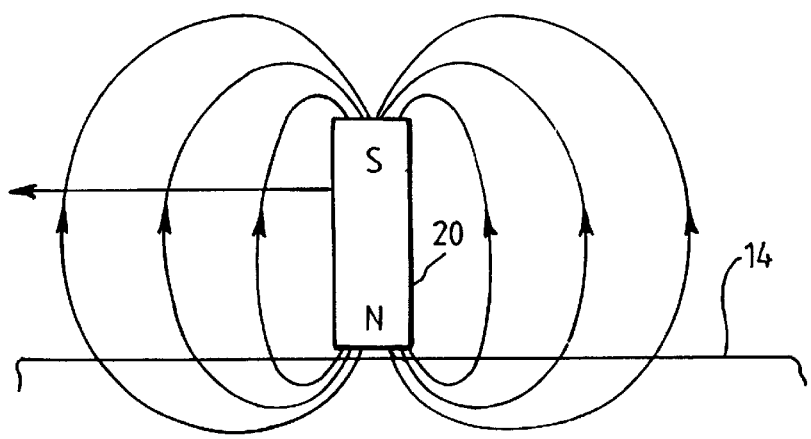
FIG. 4.
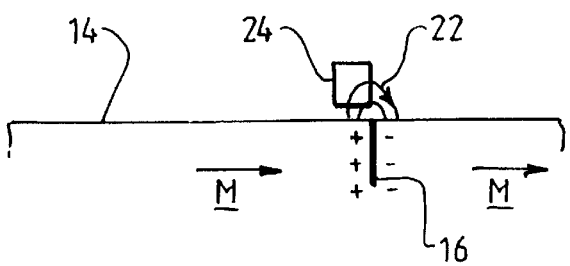

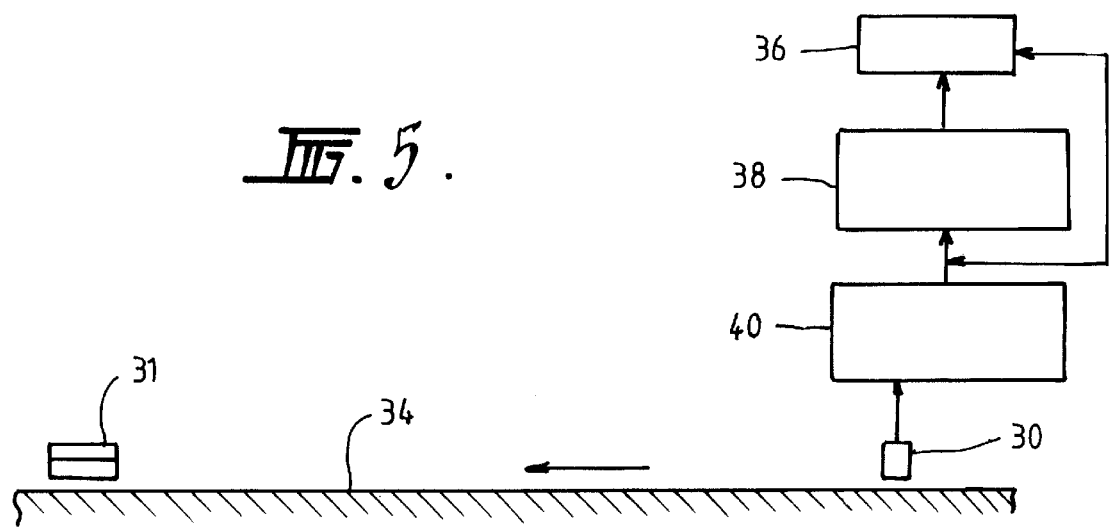
FIG. 5.
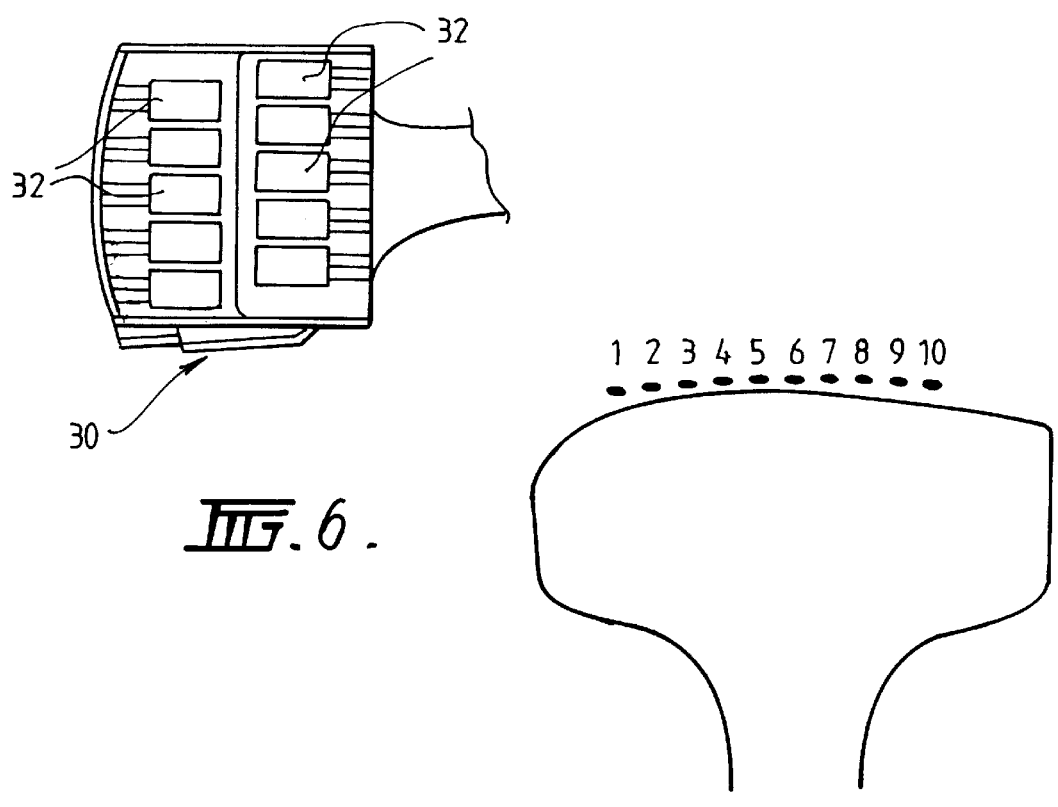
FIG. 6.
FIG. 11.

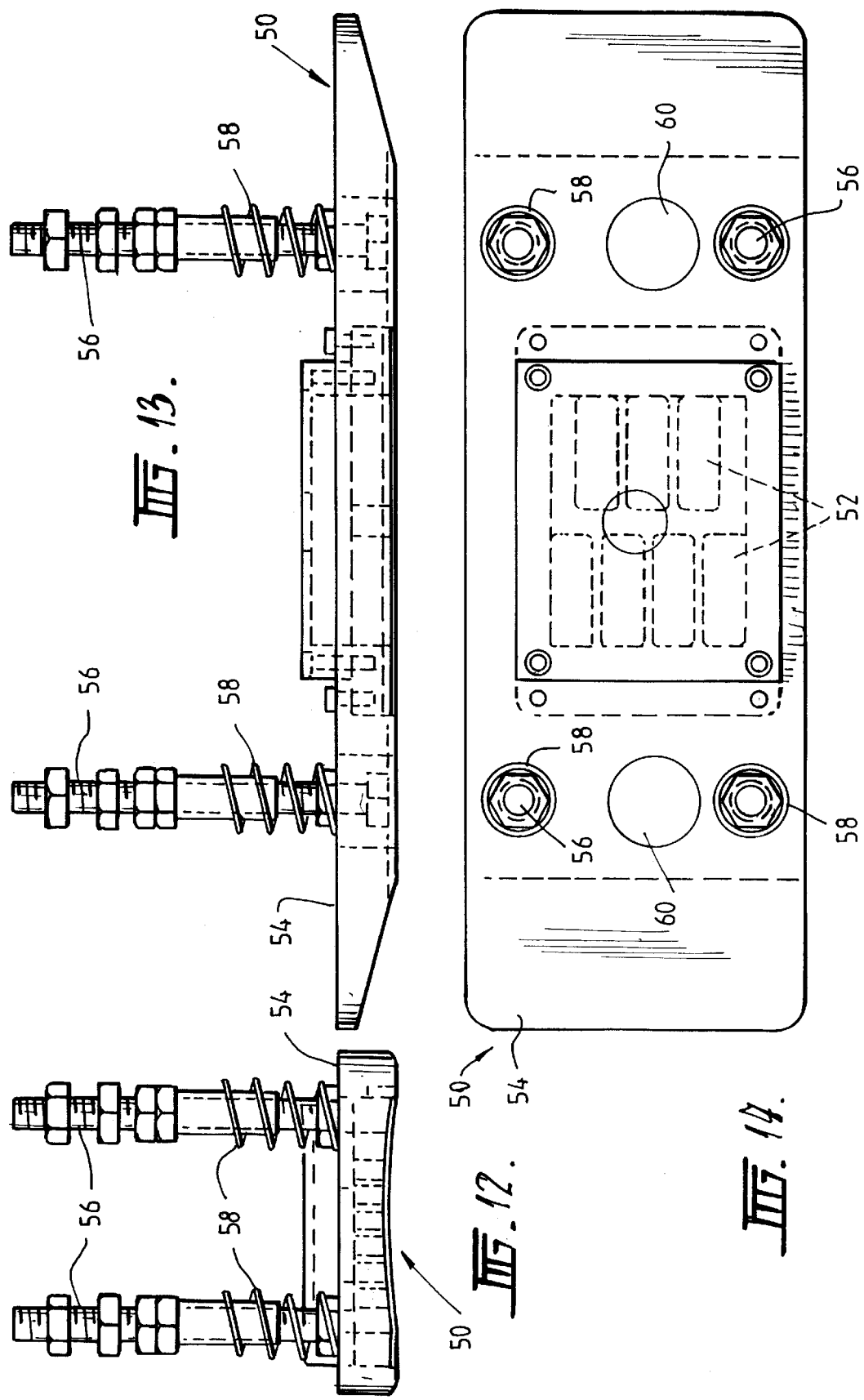

MAGNETIC DETECTION OF DISCONTINUITIES IN RAILWAY RAILS USING HALL EFFECT SENSORS

FIELD OF THE INVENTION

The present invention relates to a method and apparatus for magnetically detecting discontinuities in magnetic materials and relates particularly, though not exclusively, to such a method and apparatus for detecting surface fatigue cracks in steel rails of railway track.

BACKGROUND TO THE INVENTION

Surface fatigue cracks form in the running surface material of rail heads due to the accumulative effect of wheel loading stresses in the region of the rail-wheel interface. If surface cracks propagate over a sufficient distance along the rails, spalling of the rail surface material occurs which greatly reduces the service life of the railway rails. It is common practice in the management of railway tracks to periodically grind the running surface material down to restore the rail profile as close as possible to the desired shape and to prolong the service life of the rail. The frequency of grinding may be determined by such factors as profile degradation, maximum crack depth and crack geometry, the exhaustion of ductility of the surface material and grinder scheduling limitations. It is therefore desirable to be able to monitor the extent and severity of surface fatigue cracking across and along the running surfaces of the rail heads in order to determine appropriate grinding strategies.

Surface fatigue cracks rarely result in catastrophic failure of the rail. Rail failure is more closely related to internal defects such as transverse defects (TDs), sometimes called "rolling contact fatigue" defects. The most commonly employed non-destructive method for detecting such internal defects is ultrasonic flaw detection. Railway rails are regularly monitored using ultrasonic detectors applied to the rail heads in an attempt to detect the presence of internal defects before catastrophic failure occurs, which may lead to derailment. However, it is thought that surface fatigue cracks hide or mask the presence of internal defects from ultrasonic detection so that the internal defects may not be detected in time. In the USA, the failure to detect internal rail flaws, which led to a major derailment of a train, was blamed on the presence of rail surface fatigue defects. (National Transportation Safety Board (1994), Derailment of Burlington Northern freight train No. 01-142-30 and release of hazardous materials in the town of Superior, Wis., Jun. 30, 1992. Hazardous Materials Accident Report NTSB/HZM-94/01. Washington DC., Report Number PB94-917003). This illustrates the importance of being able to reliably detect the presence of surface fatigue cracks in railway rails.

Magnetic stray flux techniques in non-destructive testing for defects in ferromagnetic materials are well known. The test object is typically magnetised by an imposed magnetic field and the magnetic flux generally stays largely within the object unless it encounters cracks, flaws or other discontinuities in the metal object. At the location of such discontinuities a portion of the magnetic flux is expelled into the air as stray flux. The discontinuity in the metal object results in a region of increased resistance to the flux density which causes some of the flux to deviate around the discontinuity, a portion of which "strays" into the surrounding air. Various techniques have been developed for measuring this stray flux in order to infer the presence of defects in the object.

U.S. Pat. No. 4,792,755 discloses one such prior art apparatus and method for non-destructive testing of metal tubes having surfaces adjoining each other along edges or corners. An imposed magnetic field is generated in the tube between two magnetic pole shoes using an electromagnet. Stray flux is detected using a plurality of magnetic field sensors, typically Hall probes, connected in pairs to a multiplexer by way of differential amplifiers. Stray flux values are measured and subtracted from stored reference values and the results examined in a threshold value discriminator to ascertain whether a preset threshold value, which is indicative of the existence of a structural fault, is exceeded.

One disadvantage of the known prior art magnetic techniques for detecting defects lies in the methods employed for magnetising the test object. Generally the test object is magnetised by an imposed magnetic field generated by the two poles of a magnet (permanent magnet or electromagnet) positioned either side of a detector. Alternatively the imposed magnetic field is generated or induced by passing an electric current through the test object. The difficulty with using an imposed magnetic field is the increased complexity it necessitates in the engineering of the structure and arrangement of the test apparatus. In the case where an electromagnet or the induced magnetic field technique is employed, an electric current source with the appropriate control circuitry must also be provided. These prior art magnetisation techniques do not easily lend themselves to high speed testing of rails installed in railway tracks.

The present invention was developed with a view to providing a simple and effective magnetic technique for assessing rail surface fatigue in railway tracks which is capable of deployment along the tracks at high velocities. However it will be understood that the technique may have wider application and is not necessarily limited to measuring rail surface fatigue.

The term "magnetic material" is used throughout the specification to describe materials, such as iron and steel, characterised by the property known as spontaneous magnetisation and capable of acquiring remanent magnetisation after exposure to and subsequent removal of an applied magnetic field.

SUMMARY OF THE INVENTION

According to one aspect of the present invention there is provided a method for magnetically detecting surface defects in a magnetic material, the method comprising the steps of:

magnetising the magnetic material in an area of interest by passing an applied magnetic field over the area of interest, leaving a remanent magnetic field; and, sensing stray flux generated in the vicinity of surface defects in the magnetic material by the remanent magnetic field after the applied magnetic field has been removed whereby, in use, the presence of surface defects in the magnetic material can be detected.

Typically said step of magnetising the magnetic material involves touch magnetisation using a permanent magnet. Touch magnetisation requires one magnetic pole of the permanent magnet to be moved parallel to and in close proximity to the surface of the object which is to be left in a state of remanent magnetisation.

Preferably said step of sensing stray flux involves passing a magnetic field sensing means over a surface of the magnetic material in the area of interest and measuring fluctuations in the remanent magnetic field strength in the vicinity of said surface defects.

According to another aspect of the present invention there is provided an apparatus for magnetically detecting surface defects in a magnetic material, the apparatus comprising:

magnetic field generating means for magnetising the magnetic material in an area of interest by passing an applied magnetic field over the area of interest, leaving a remanent magnetic field; and, magnetic field sensing means for sensing stray flux generated in the vicinity of surface defects in the magnetic material by the remanent magnetic field after the applied magnetic field is removed whereby, in use, the presence of surface defects in the magnetic material can be detected.

In one embodiment said magnetic field generating means is a permanent magnet, for example, a plurality of high energy Neodymium Iron Boron (Nd—Fe—B) permanent magnets stacked one on top of the other. An electromagnet with a suitable configuration could also be used. The magnetic sensing means may, for example, be a Hall effect sensor which is sufficiently sensitive to detect fluctuations in the magnetic field strength caused by surface defects in the magnetic material. Alternatively, the magnetic sensing means may be a detector of the inductive type.

Typically the apparatus is used for detecting surface defects in the magnetic material of a railway rail, although it may also be possible to detect internal defects in some applications. Preferably said magnetic field generating means and magnetic field sensing means are mounted on a carriage for transport over a surface of the magnetic material, said magnetic field generating means being mounted ahead of the magnetic field sensing means when the carriage is moving in a forwards direction.

Advantageously said magnetic field sensing means comprises a plurality of sensors arranged side by side transverse to the direction of movement of the carriage, each sensor sensing fluctuations in the magnetic field strength in the direction of movement each within a relatively narrow strip whereby, in use, said plurality of sensors can also provide an indication of variations in the magnitude of fluctuations over a band of adjacent strips in the transverse direction.

A preferred embodiment of the method and apparatus is used for high speed detection of surface cracks in railway rails.

Advantageously said magnetic field generating means is a permanent magnet mounted for transport over the surface of a rail head, typically spaced above the rail head between 1 mm and 20 mm, more typically between 3 mm and 15 mm above the rail head. Preferably said magnetic field sensing means comprises a sensor head with a curvature matched to a typical rail head profile, and having a plurality of Hall probes mounted side by side to cover a transverse region over the rail head extending from the gauge side to the field side of the rail head.

In a preferred embodiment, seven Hall probes spaced at predetermined intervals are provided, thus covering a substantial portion of the rail head, to produce a seven channel sensor head. The signals from the sensor may be directly logged or converted to root mean square (RMS) values averaged over a distance along the rail and then logged.

Preferably said sensor head is mounted for transport over the surface of a rail head, spaced away from said magnetic field generating means by at least 0.25 meter, more typically 0.5 meter. Preferably the sensor head is spaced above the rail head between 0.5 mm and 3 mm, more preferably between 1.5 mm and 2.0 mm.

BRIEF DESCRIPTION OF THE DRAWINGS

In order to facilitate a better understanding of the nature of the invention a preferred embodiment of the apparatus and method of magnetically detecting discontinuities in magnetic materials will now be described in detail, by way of example only, with reference to the accompanying drawings, in which:

FIG. 3 illustrates a prior art magnetisation technique;

FIG. 4 illustrates one embodiment of a remanent magnetisation technique in accordance with the invention;

FIG. 5 illustrates schematically one embodiment of the method and apparatus for detecting discontinuities in metal objects in accordance with the invention;

FIG. 6 illustrates one embodiment of a multi-channel sensor head employed in the method and apparatus of FIG. 5;

FIG. 11 illustrates the relative lateral positions of the Hall probes in the sensor head above the rail head;

FIG. 12 is an end view of a second embodiment of a multi-channel sensor head employed in the apparatus and method;

FIG. 13 is a side view of the sensor head of FIG. 12; and,

FIG. 14 is a bottom plan view of the sensor head of FIG. 12.

DETAILED DESCRIPTION OF PREFERRED EMBODIMENTS

Figure 1:
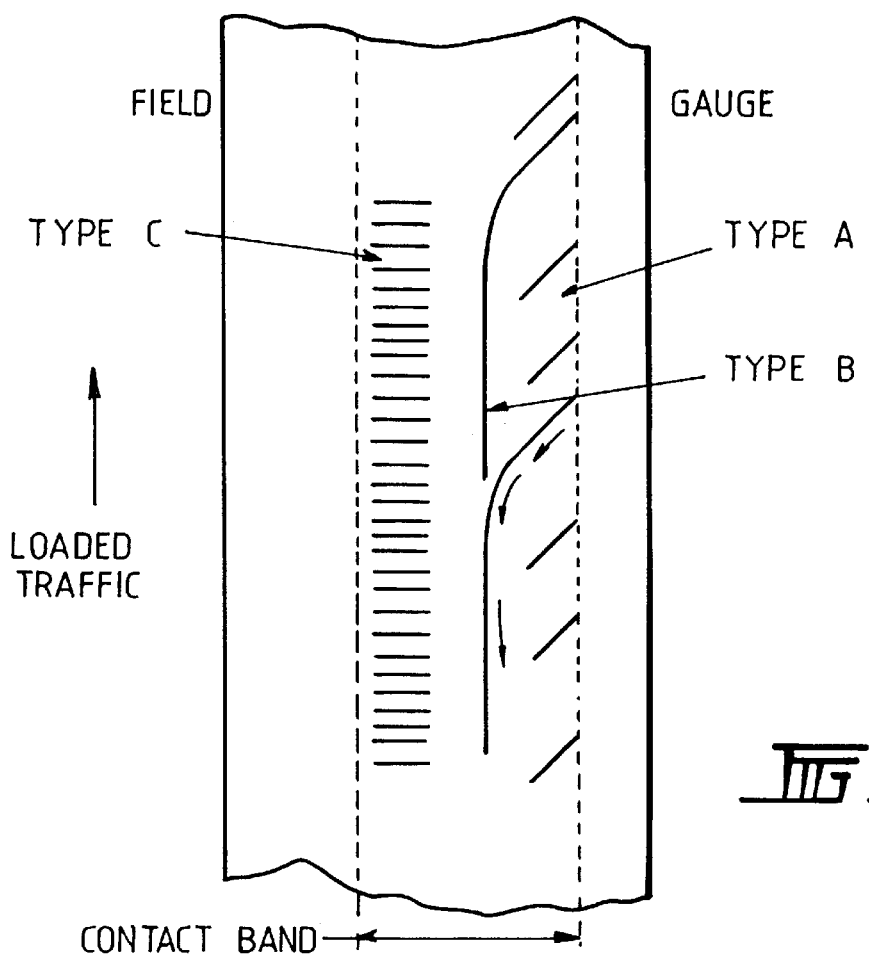
FIG. 1 illustrates schematically the type of surface fatigue cracks that can occur in rail.

Investigations into the mechanism and extent of rail surface fatigue in tangent railway track operated by Hamersley Iron Pty Ltd in Western Australia, have identified lateral shear of the rail surface material as the predominant force in the propagation of the most severe type of surface fatigue crack. Shear cracking typically occurs on the gauge side edge of the contact band (see FIG. 1), driven by the high shear deformations present in this area. Cracks initiate and grow, for the most part, in the first 5.0 mm or so in depth of the rail head material, when the material's ductility is exhausted. The mechanism driving crack growth is the passage of railway wheels, particularly the passage of more heavily loaded wheels with poor wheel tread profiles.

The cracks begin as the Type A variety (see FIG. 1), growing down into the rail head material in the direction of loaded traffic and across the rail at an oblique angle. When the Type A cracks reach the centre of the contact band, only lateral shear is present to drive their growth, and hence they turn into the longitudinal orientation to form Type B cracks. Type B cracks grow downwards towards the field side of the rail head (see FIG. 2). The lateral shear that drives Type B growth is mostly caused by wheel set yaw, which is greatest for curves, and significant for tangents where unstable tracking occurs.

Type A cracks appear to grow to about 1 mm in depth soon after initiation. As the Type A cracks grow on the surface in the lateral and longitudinal directions, their depth continues to increase, such that they have typically reached a depth of about 1.5 mm–2.0 mm by the time they start to turn into Type B cracks. At this point, it appears the downward growth of the crack slows (with respect to accumulated wheel pass-tonnes) and the Type A portion of the crack may not grow any deeper. Hence Type B cracks are typically about 1.5 mm–2.0 mm deep when they start growing along the rail.

Longitudinal growth of the Type B cracks may be very rapid and it is possible for a Type B crack to propagate over relatively long distances along the rail once it has been established.

Figure 2:
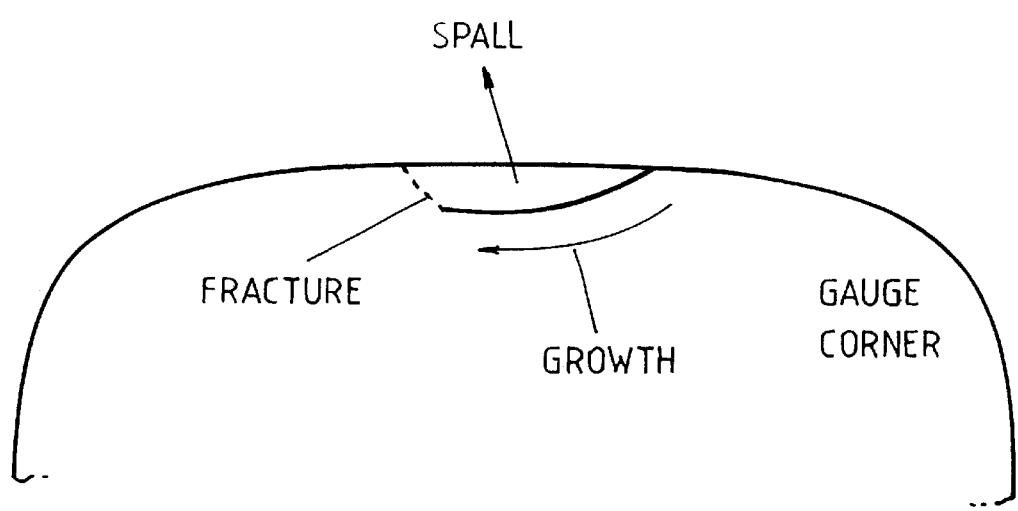
FIG. 2 illustrates schematically the type of sub-surface growth of cracks in rail that can lead to spalling.

At some point during the horizontal growth of Type B cracks, a second crack initiates from the surface on the field side, and runs down to intersect the Type B crack, thus producing a spall (see FIG. 2). Downward growth of Type B cracks typically continues to a depth of approximately 3.0 mm before spalling occurs. In view of their longitudinal orientation and the tendency to bend into the horizontal plane, it is the Type B cracks that lead to continuous spalling of the rail's running surface in tangent track. Large Type A cracks can cause isolated spalling, which though not as serious as that caused by Type B cracks, may still require corrective grinding. Large Type A cracks are also the precursor to Type B cracks.

In order to facilitate an assessment of the severity of rail surface fatigue along the railway tracks, and to enable an appropriate grinding strategy to be implemented, a technique for magnetically detecting surface fatigue cracks was developed. As noted above, magnetic stray flux techniques are well-known in the non-destructive testing for defects in ferromagnetic objects. It was not known whether it was feasible to detect magnetic flux leakage from rails with surface fatigue cracks. The present invention is based on the discovery that not only is such a magnetic technique feasible, but that remarkably accurate and reproducible results can be obtained using a remanent magnetic field generated by prior magnetisation of the rail. Through trial and experimentation in the laboratory it was found that the best results were obtained using a remanent magnetisation technique with detection of magnetic flux leakage.

FIG. 3 illustrates a magnetisation technique which was considered for use in the detection of surface fatigue. This technique involves imposing a magnetic field on the test object (in this case rail) by positioning the two poles of a magnet 10 (permanent or electro) either side of a detector 12 and moving the whole assembly along the surface of interest (in this case the running surface of the rail head). The presence of a crack 16 causes some of the flux to "leak" into the air as stray flux 18 which can be measured by detector 12.

A more efficient magnetisation technique is shown in FIG. 4, which illustrates a preferred embodiment of the remanent magnetisation technique according to the invention. In the illustrated embodiment a remanent magnetic field is produced in the magnetic material (rail) by sliding a magnet 20 along the surface 14 with one pole facing towards the surface. This is a well known method of magnetising a ferrous object, sometimes referred to as magnetisation by touch. When the magnet 20 is removed from the area of interest a magnetisation remains within the material which is known as induced remanent magnetisation induction. After magnetisation, stray flux 22 produced by the remanent magnetic field at the location of a crack 16 may be detected by detector 24.

Laboratory measurements with a Gaussmeter demonstrated that there were measurable levels of remanent magnetic field normal to the rail surface at surface fatigue cracks. The remanent magnetic field was produced by touch magnetisation using two rare earth permanent magnets (Neodymium Iron Boron, Nd—Fe—B) as the magnetisation source. An inexpensive Hall effect integrated circuit (hereafter referred to as a Hall probe) was sourced, and the field above the rail surface was mapped. A suitable Hall probe with sufficient sensitivity is a Linear Output Hall Effect Transducer (LOHET) integrated circuit. A ceramic tile on which the IC is mounted is 16 mm×8 mm, with a maximum device thickness of about 3 mm. The LOHET device is sensitive to the magnetic field normal to the plane of the ceramic tile, with the area of maximum sensitivity being about 5mm from the trailing end. The device specifications are as follows:

| Span | ±400 Gauss |
| --- | --- |
| Sensitivity | 0.625 mV/V/Gauss |
| Supply Voltage | 8–16 V |
| Response Time | 3 µs |
| Temperature Coefficient | 0.08%/° C. |

Figure 7:
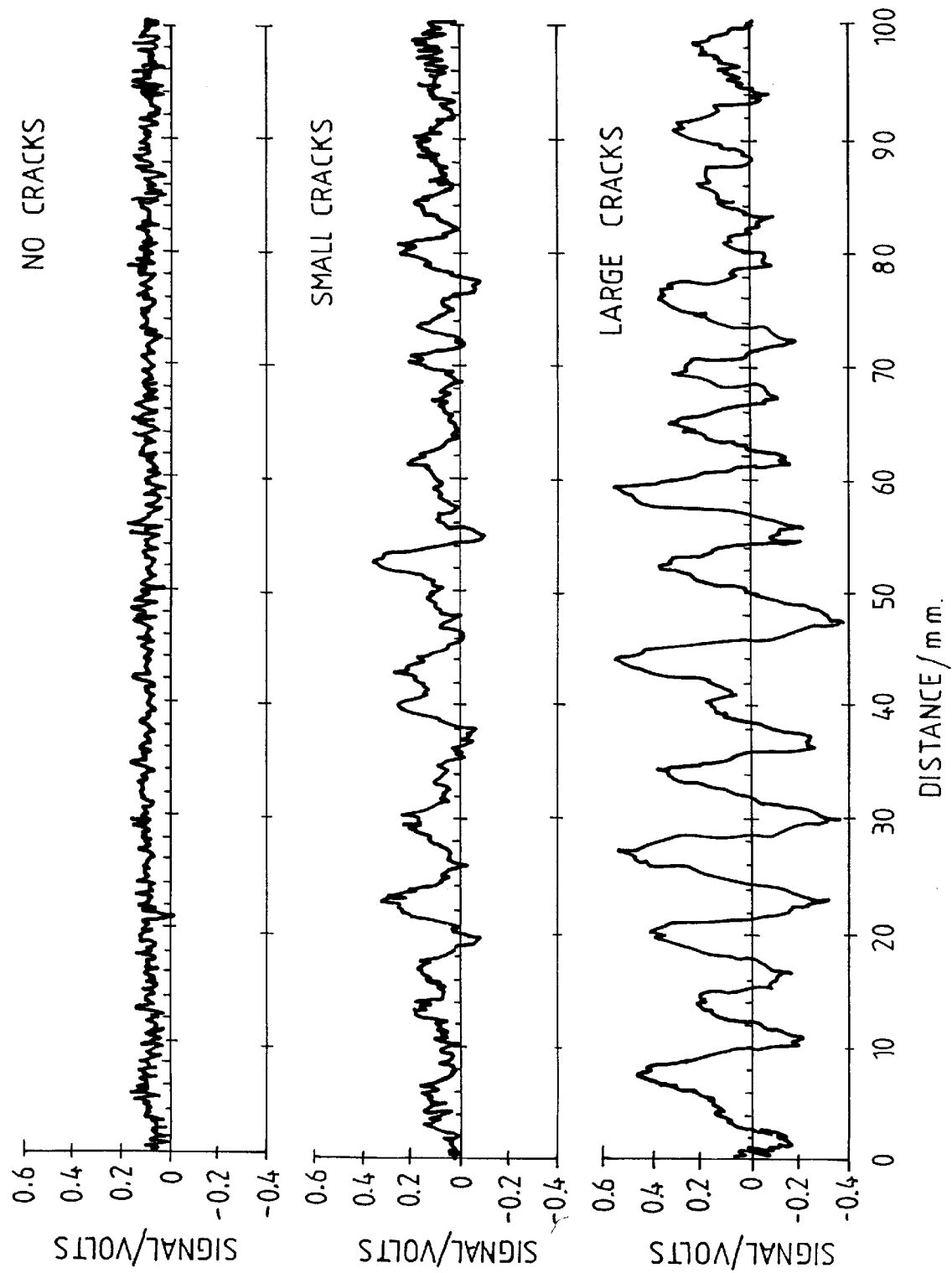
FIG. 7 illustrates graphically the amplified output of a Hall probe of the kind employed in the sensor head of FIG. 6.

With this Hall probe, the relative field strengths at various heights above a previously magnetised rail sample were measured, covering rail surface with large widely spaced cracks, small closely spaced cracks and no cracks. Results for a detector height of 0.5 mm are illustrated graphically in FIG. 7. These results demonstrated that the signal fluctuations for large widely spaced cracks correspond one to one with individual surface cracks. However, for small closely spaced cracks the signal levels were reduced and the number of peaks did not necessarily correlate directly with the number of cracks. These measurements showed that signal magnitude decreases with increasing sensor height and that the magnitude of the remanent magnetic field is below the limit of detection above a certain height. As may be understood from theoretical analysis the size and spacing of the cracks determines the maximum sensor height above which the cracks will not be reliably detected.

For large widely spaced cracks, (typical of Type A cracks in rails of tangent track), useable signals were detected with the sensor typically up to 3 mm above the rail head surface, but signal quality decreased significantly above 2 mm. For small closely spaced cracks, (typical of Type A cracks in rails of curved track), the sensor was preferably kept 1.5 mm or less above the rail head surface to produce signals above background noise levels. Severe Type B cracks produced signal levels equal to or greater than those produced by large Type A cracks, but at a lower frequency (typically one third), presumably because of the different crack geometry. The results were shown to be independent of repeat magnetisation of the same section of rail.

A trolley suitable for high speed operation was constructed, with two larger magnetising magnets 31 mounted at a height of approximately 4 mm–6 mm above the rail head surface. A series of trials were conducted with the high speed trolley, using the apparatus illustrated schematically in FIG. 5. In order to classify the severity of surface fatigue, information is needed about the distribution of cracks across the rail head in a direction transverse to the direction of travel. A ten channel sensor head 30 was constructed with a curvature matched to a typical tangent rail profile, as illustrated in FIG. 6. Ten LOHET sensors 32 were mounted in two rows, spaced every 5 mm, thus covering a 45 mm wide band across the rail head 34. The output signals from the sensors 32 are amplifiers 40 and could either be logged directly using data logger 36, or be electronically converted to averaged RMS values using RMS conversion circuit 38 and then logged in data logger 36. Logging of averaged RMS values instead of the direct output signals greatly reduces the volume of data to be logged. Two RMS averaging times were available: 45 milliseconds for high speed and 220 milliseconds for low speed. The system was tested at low speed (approximately 5 km/h) on a tangent track leading into a left hand curve, and at high speed (80 km/h) on a tangent track, slowing to 30 km/h into a left hand curve. The sensor head 30 was positioned approximately directly over the rail centre line and at a height of approximately 1.5 mm above the rail surface in the tangent section, with channel 1 located over the gauge corner.

The RMS output signals from the 10 channels were logged at 10 Hz at low speed on the tangent track, and at 100 Hz at high speed along the tangent track and at 50 Hz in the curve. The output signals gave an excellent representation of the surface fatigue condition of the rail in the tangent track sections, with cyclic variations in rail surface condition, due to the hunting behaviour of ore cars which occurs primarily on the tangent tracks, these variations being clearly visible by the naked eye. It was observed that surface fatigue severity reached a maximum at approximately every 20–25 meters. In these regions of severe surface fatigue, strong signals were generated on channels 1 to 3, with moderate signals on channel 4 and background noise on channels 5 to 10. The signals on channels 1 to 3 are representative of surface fatigue cracks on the gauge side of the rail head, extending in towards the centre of the rail head's top surface in the worst areas. Marker magnets were placed on the field side of the rail head every 50 meters to allow interpolation of position produced full scale signals on all channels every 50 meters. As the trolley moved from the tangent track into the transition spiral and true circular curve the output signal's levels reduced significantly. Examination of the trolley in the true circular curve revealed that the sensor-rail gap had increased significantly on the gauge side, due to increased gauge side wear of this curve's high rail. This, together with the change in crack morphology to fine closely spaced cracks of the type usually observed in curves, would be expected to reduce the signal levels from the gauge side sensors.

Figure 8:
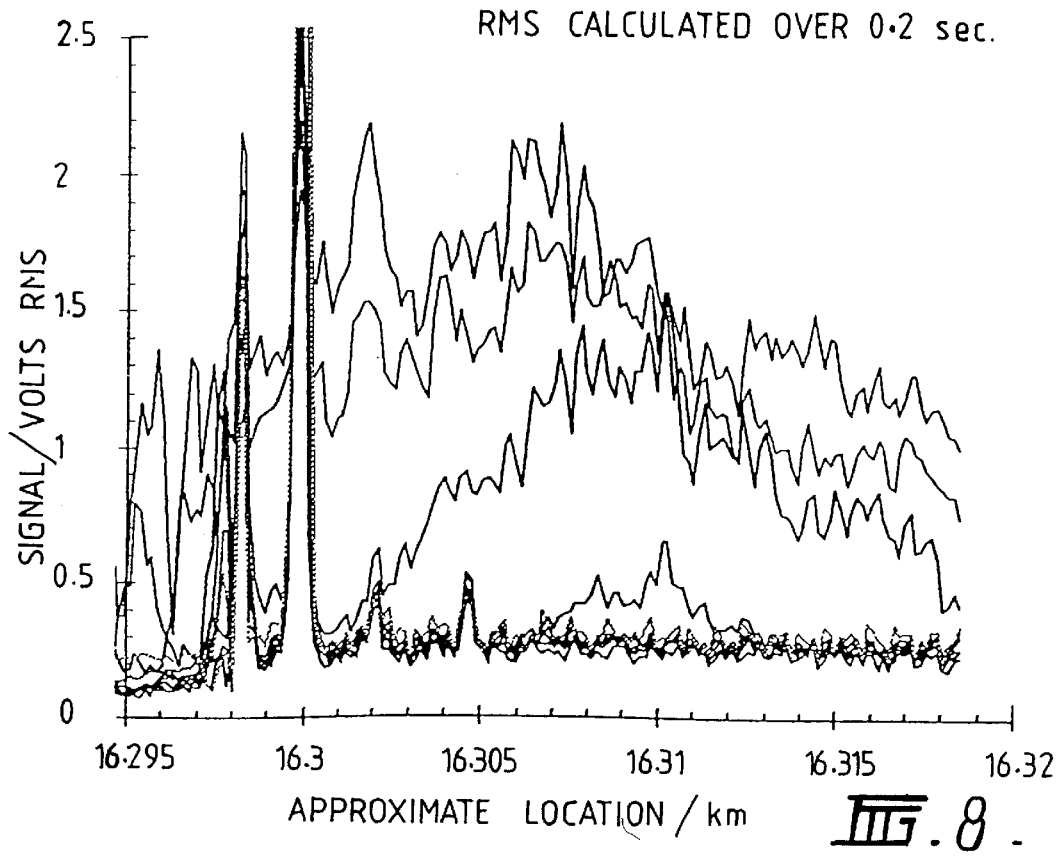
FIG. 8 illustrates graphically RMS Hall probe outputs from the multi-channel sensor head of FIG. 6.
Figure 9:
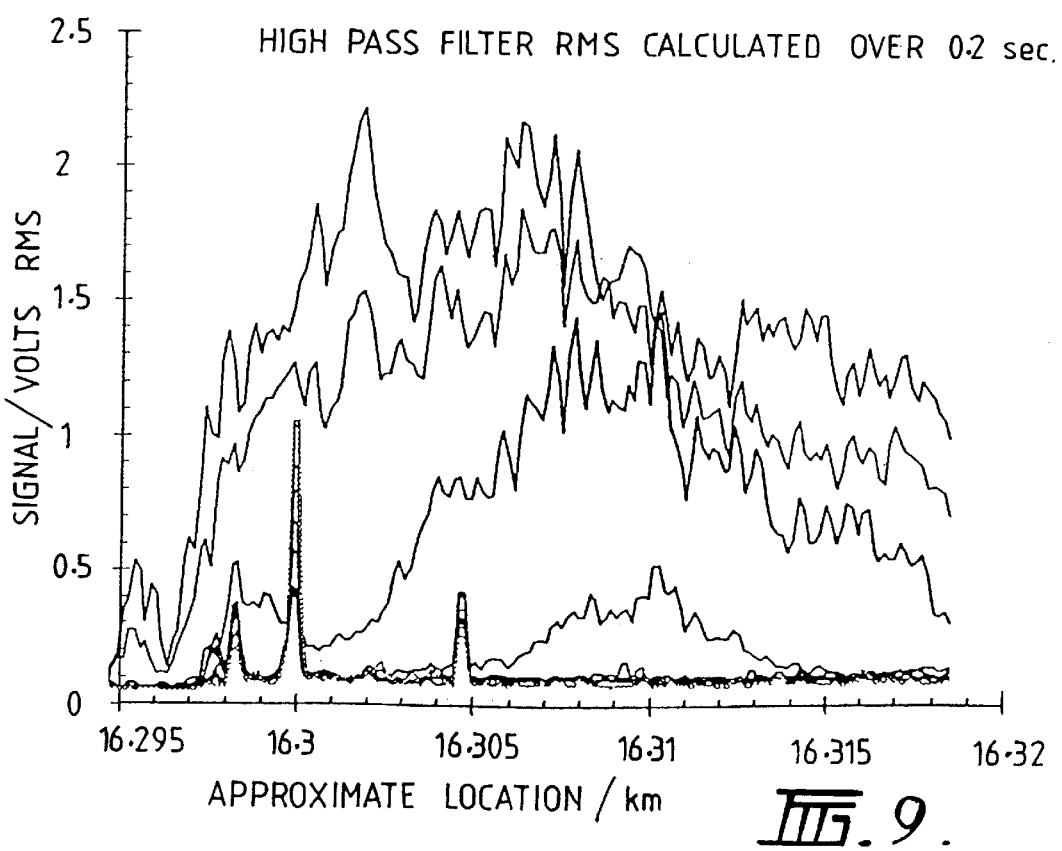
FIG. 9 illustrates graphically the RMS Hall probe outputs of FIG. 8 after high pass filtering to reduce background noise levels.

The sensor output signals were also logged directly (after amplification, but before the RMS conversion circuit) over short sections of the curve and spiral with the sensor head tilted to better match the different rail shape. This allowed gauge side and field side channels to be distinguished more readily. The direct output signals were also logged over a short section of the tangent track for filtering analysis. The sensor amplifiers used for the high speed trials had a band-width of approximately 10 Hz to 8 kHz. Although modification of the trolley wheels reduced the vibration induced signals by an order of magnitude, there were still significant vibration induced signals contributing to the background RMS levels. In practice, the magnetic detection system would be operated at speeds of 40–80 km/h, where cracks spaced at approximately 5 mm–10 mm intervals would give signal frequencies of 1–4 kHz. The wheel induced vibrations occur at frequencies from approximately 10 to 100 Hz. Consequently, high pass filtering at approximately 50 Hz can be used to improve resolution of surface fatigue detail without affecting output signals generated by cracks at spacings of 100 mm or less. FIGS. 8 and 9 illustrate graphically the RMS output signals on the 10 channels with and without high pass filtering respectively. As can be clearly seen in FIG. 9, high pass filtering has reduced the background RMS levels, revealing more detail on channel 4 in particular, than can be observed in the unfiltered signals. The signal to noise ratio on all channels has been doubled as a result of high pass filtering. High pass filtering was performed mathematically on the sample of direct sensor outputs logged on the tangent track (referred to above) and then converted to RMS.

For the high speed runs (80 km/h) along the tangent track the RMS conversion circuits were set to a 45 millisecond averaging time. Marker magnets were placed on the field side of the rail head at 500 meter intervals. Two runs were made, the first run with the sensor head set at a height of approximately 2 mm above the rail head surface, and the second run (several hours later) with the sensor head height set at approximately 1 mm–1.5 mm above the rail head surface. The two runs along the tangent track gave identical results, except that the signal levels were higher for the second run (twice the levels of the first run), as a consequence of the reduced sensor height on the second run. The rail surface condition was photographed at selected locations along the tangent and comparison of the actual surface condition as photographed to the signals in the vicinity of these locations revealed excellent correlation of the signals and the location of the surface fatigue cracks. Even the presence of very small Type A cracks was unequivocally detected.

FIGS. 12, 13 and 14 illustrate a second embodiment of a multi sensor head 50, which employs seven Hall probe sensors 52 mounted in two rows as illustrated in FIG. 14. In practice, it was found with the ten channel sensor head 30 of FIG. 6 that the signal levels on channels 1 and 9 were relatively small and contributed little to the detection of surface defects across the width of the rail head. As can be seen most clearly in FIGS. 12 and 13 the Hall probe sensors 52 are mounted within an enclosure provided within a support plate 54, which is in turn mounted to a carriage (not shown) for transport over the surface of the rail head. Support plate 54 is typically manufactured from aluminium alloy plate and is suspended from the carriage by four stainless steel bolts 56 with four compression springs 58 for shock absorbing during minor impact. As can be seen most clearly in FIG. 12, the transverse profile of the sensor head 50 is shaped to match the transverse profile of the upper surface of the rail head.

In order to compensate for the variations in magnetic signal strength due to variations in the height of the sensor head above the rail, two proximity sensors 60 were incorporated into the sensor head 50. Each proximity sensor has an output of 0–10 volt for a range of 2–4 mm. A voltage divider is used to reduce the output to 0–5 volt before logging. On the basis of experimental measurements, the multiplication factor required to convert a signal at a height Xmm above the surface, $V_x$, to a value at 1 mm above the surface, $V_1$, is $(X+1)/2$. In the illustrated embodiment, the proximity sensors 60 are recessed 1.75 mm relative to the lower surface of the aluminium frame of the sensor head 50, and the Hall effect ICs by 0.75 mm (including shim thickness 0.25 mm). Thus, for this embodiment the relationship between the proximity sensor output $V_p$ and the height X in millimeters of the Hall effect ICs above the rail is:

$$x = 2/5 * V_p + 1$$

The output of the proximity sensors 60 was logged at the same frequency as the magnetic signals. Ideally, the raw magnetic signals should be compensated at each location that the magnetic signals are logged using the corresponding measurement of the height of the sensor. However, this exercise is not straight-forward partly because the magnetic data is logged as average RMS values. It was shown, however, that adequate compensation can be obtained by using an effective height X', where X' is the average of the heights corresponding to the SF' values employed in the calculation of surface fatigue severity.

Figure 10:
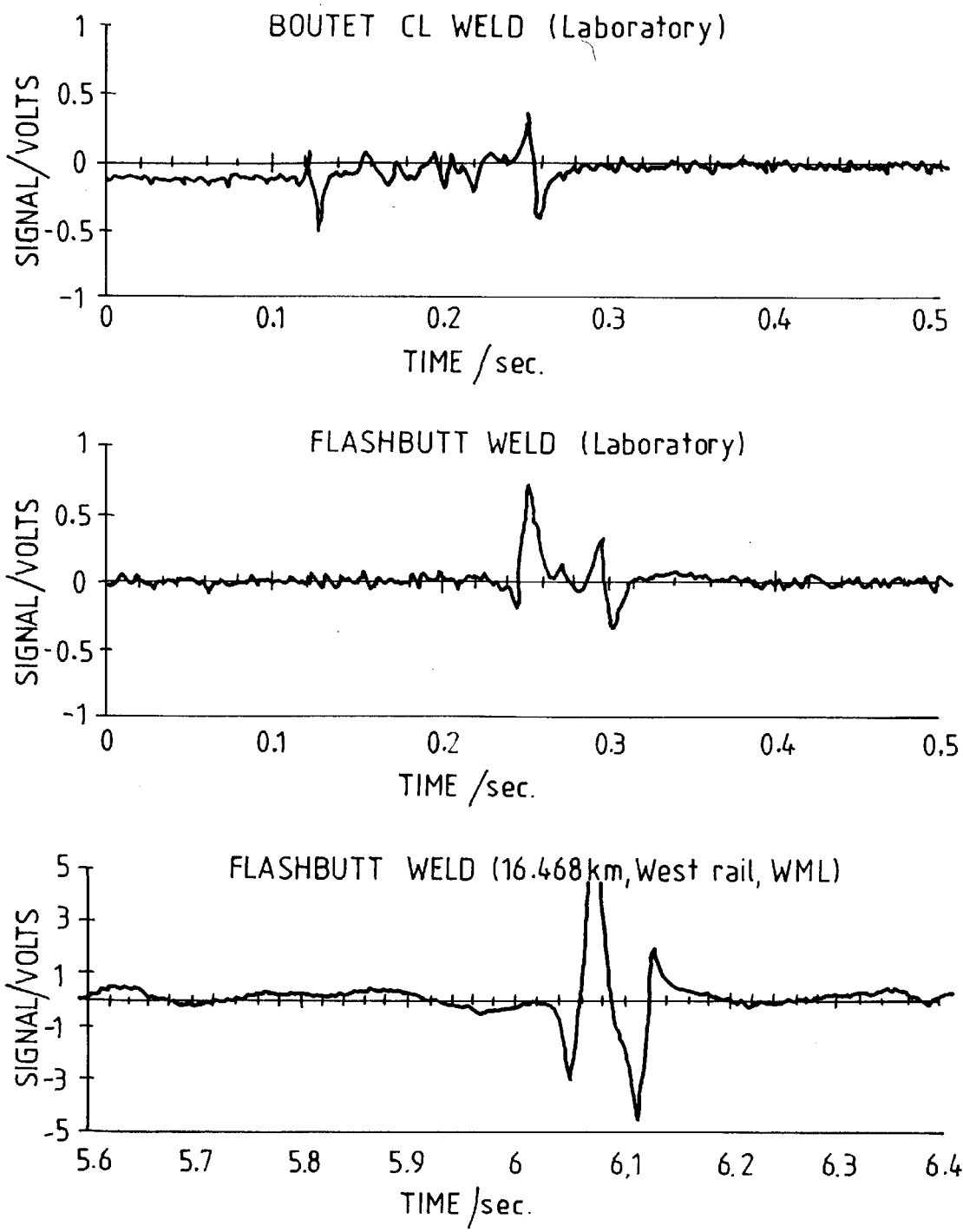
FIG. 10 illustrates graphically Hall probe outputs indicating magnetic field variations across rail welds.

The RMS output signals on all or most channels registered isolated large peaks at various locations along the section of rail tested, in addition to those caused by the marker magnets. By measuring the location of all welds along the test section, it was shown that most of these peaks corresponded to the location of welds (flashbutt and field welds). Examination of the remaining locations revealed minor rail lower gauge face irregularities which would have impacted the trolley's guidance wheels, causing the trolley to jump and thus producing a large variation in sensor-rail gap. The direct sensor output signal from a flashbutt weld in track is compared to the signals measured in the laboratory for a flashbutt weld and a Boutet CL field weld in FIG. 10. From these results it is apparent that the planar spheroidised regions on both sides of the welds (corresponding to the locations of minimum hardness in the weld's heat affected zones) act as large magnetic discontinuities, because the magnetic permeability of the spheroidised regions is significantly different from that of the parent rail. Clearly therefore, if desired the remanent magnetisation technique in accordance with the invention may be used to map the locations of all welds or other similar discontinuities in metal objects.

From the above description of several embodiments of the magnetic detection system using a remanent magnetisation technique it will be apparent that the system may be readily modified for permanent fixture on a conventional track recording vehicle (TRV) for use in routinely monitoring the surface fatigue severity along a railway. The mathematical relationships between surface fatigue severity and the RMS outputs from the system may be determined, and these algorithms may then be encoded in post-processing software. The software can output indications of surface fatigue severity for use in scheduling of rail grinding activities designed to minimise the total cost of rail-wheel management.

An algorithm was developed to translate the RMS output values of the ten Hall effect IC's of the sensor head into a single value representing the severity of the surface fatigue. As noted above, the nature of surface fatigue cracking varies across the head of the rail in a characteristic manner, and therefore the output signal levels of all channels of the sensor head are not equally important. The relative positions of the respective sensors for each of channels 1 to 10 on the rail head is illustrated in FIG. 11. Therefore, it is not possible to simply use the sum of the values of all the channels as a measure of surface fatigue severity. For this reason, a suitable way of combining the information from the ten channels was developed by comparing the data from a series of test locations that were judged to have increasing levels of surface fatigue severity.

As a first step, the values of the individual channels were considered separately and it was found that the correlation with surface fatigue was stronger for channels corresponding to the centre of the rail head, in particular channel 4. By further experimentation with different combinations of the channels, it was determined that the correlation between the signal value of channel 4 and rail surface fatigue was improved by the addition of the values of channels 3, 5 and 6 weighted according to the following algorithm:

$$SF'=Ch4+2(Ch3+Ch5+Ch6)$$

where SF' is a single value representing the severity of the surface fatigue at a particular location along the rail head. The correlation may be improved by changing the weighting given to the additional channels or by using a different combination of channels.

It will be apparent that the remanent stray field technique for detecting magnetic discontinuities in rail and other magnetic materials has significant advantages over prior art stray flux techniques, including the following advantages:

(i) interference due to relative movement of the magnetic field generating apparatus and the sensors is virtually eliminated in view of the wide spacing between the two;

(ii) the technique has been proven to work at speeds up to 80 km/h, and there is no fundamental limitation for operating at speeds up to several hundred kilometers per hour provided the sensors can be maintained in sufficiently close proximity to the surface of the magnetic material with minimal vibration;

(iii) the system utilises simple, inexpensive hardware for the magnetisation of the metal object, sensing of stray flux and processing of the output signals;

(iv) the remanent magnetisation technique produces highly reproducible results;

(v) the distribution of surface fatigue cracks or other magnetic discontinuities across a rail head may be determined using a multiple sensor head;

(vi) the apparatus and method can be readily modified for incorporation into an operating system (such as a conventional track recording vehicle) for routinely monitoring rail surface fatigue severity of an entire railway system.

Numerous variations and modifications will suggest themselves to persons skilled in the relevant arts, in addition to those already described, without departing from the basic inventive concepts. For example, the shape or configuration of the multi-sensor head as well as the number and location of detectors may be modified to suit the particular application and/or the transverse profile of the surface of the magnetic material being tested. Furthermore, depending on the nature of the magnetic material being tested, the pre-magnetisation used to produce a remanent magnetic field in the object may be effected in various ways other than that described above. Touch magnetisation is the preferred method for the detection of surface fatigue cracks in rail because it is simple and effective. In some applications it may be advantageous to keep the detection system stationary whilst the magnetic material is moved relative to the means for magnetisation and the detecting means. All such variations and modifications are to be considered within the scope of the present invention, the nature of which is to be determined from the foregoing description and the appended claims.

What is claimed is:

1. An apparatus for magnetically detecting surface cracks in railway rails, the apparatus comprising:

a magnetic field generator for magnetising the railway rails in an area of interest by passing an applied magnetic field over the area of interest so as to leave a remanent magnetic field in the area of interest and generate stray flux in the vicinity of surface cracks in the rail head, wherein said magnetic field generator is a permanent magnet mounted for transport over the surface of the rail head at a typical spacing above the rail head of between 3 mm and 20 mm; and a magnetic field sensor for sensing stray flux generated in the vicinity of surface cracks in the rail head by the remanent magnetic field after the applied magnetic field is removed, wherein said magnetic field sensor comprises a sensor head provided with a curvature matched to a typical rail head profile and having three to ten Hall probes mounted side by side at predetermined intervals to cover a significant portion of a transverse region over the width of the rail head to thereby produce a multi-channel sensor head, and wherein said Hall probes are sufficiently sensitive to detect fluctuations in the magnetic field strength caused by surface cracks in the rail head such that, in use, the presence of surface cracks in the rail head can be detected.

2. An apparatus for magnetically detecting surface defects as defined in claim 1, wherein said magnetic field generator is a rare earth permanent magnet.

3. An apparatus for magnetically detecting surface defects as defined in claim 2, wherein said magnetic field generator is a plurality of high energy Neodymium Iron Born (Nd—Fe—B) permanent magnets stacked one on tope of the other.

4. An apparatus for magnetically detecting surface defects as defined in claim 1, wherein said magnetic field generator and magnetic field sensor are mounted on a carriage for transport over a surface of the rail, said magnetic field generator being mounted ahead of the magnetic field sensor when the carriage is moving in a forwards direction.

5. An apparatus for magnetically detecting surface defects as defined in claim 1, wherein five to eight Hall probes spaced at predetermined intervals are provided, thus covering a significant portion of the width of the rail head, to produce a multi-channel sensor head.

6. An apparatus for magnetically detecting surface defects as defined in claim 1, wherein said sensor head is mounted for transport over the surface of a rail head, spaced away from said magnetic field generator by a sufficient distance to be out of a region of significant influence by the magnetic field generator.

7. An apparatus for magnetically detecting surface defects as defined in claim 5, wherein at least one proximity sensor is provided in said sensor head, for sensing variations in the height of the sensor head above the rail, wherein changes in signal strength from the Hall probes, caused by variations in the height of the sensor head, can be compensated for.

8. An apparatus for magnetically detecting surface cracks in railway rails, the apparatus comprising:

a magnetic field generator for magnetising the railway rails in an area of interest by passing an applied magnetic field over the area of interest so as to thereby leave a remanent magnetic field in the area of interest and generate stray flux in the vicinity of surface cracks in the rail head, wherein said magnetic field generator is a permanent magnet mounted for transport over the surface of the rail head at a typical spacing above the rail head of between 3 mm and 20 mm;

a magnetic field sensor for sensing stray flux generated in the vicinity of surface cracks in the rail head by the remanent magnetic field after the applied magnetic field is removed, wherein said magnetic field sensor comprises a sensor head provided with a curvature matched to a typical rail head profile and having three to ten Hall probes mounted side by side at predetermined intervals to cover a significant portion of a transverse region over the width of the rail head to thereby produce a multi-channel sensor head, and wherein said Hall probes are sufficiently sensitive to detect fluctuations in the magnetic field strength caused by surface cracks in the rail head such that, in use, the presence of surface cracks in the rail head can be detected; and at least one proximity sensor provided in said sensor head, for sensing variations in the height of the sensor head above the rail, said at least one proximity sensor being useable to compensate for changes in signal strength from the Hall probes caused by variations in the height of the sensor head.

* * * * *